United States Patent [19]

Takata et al.

[11] 4,438,217
[45] Mar. 20, 1984

[54] CATALYST FOR OXIDATION OF PROPYLENE

[75] Inventors: Masahiro Takata; Ryuji Aoki; Takahisa Sato, all of Himeji, Japan

[73] Assignee: Nippin Shokubai Kagako Kogyo Co., Ltd., Osaka, Japan

[21] Appl. No.: 454,611

[22] Filed: Dec. 30, 1982

[30] Foreign Application Priority Data

Jan. 6, 1982 [JP] Japan ............................. 57-406

[51] Int. Cl.³ ..................... B01J 21/08; B01J 23/78; B01J 23/84; B01J 23/88
[52] U.S. Cl. ........................... 502/205; 502/212; 502/243; 502/246; 502/263; 502/306; 502/309; 502/311; 502/527; 568/479
[58] Field of Search .................. 252/432, 437, 455 R, 252/456, 464, 468, 469, 477 R, 479

[56] References Cited

U.S. PATENT DOCUMENTS

| | | | |
|---|---|---|---|
| 2,408,164 | 9/1946 | Foster | 252/477 R |
| 3,786,000 | 1/1974 | Ono et al. | 252/469 X |
| 3,984,477 | 10/1976 | Kubo et al. | 252/437 X |
| 4,224,187 | 9/1980 | Vandersfurt | 252/437 |

Primary Examiner—W. J. Shine
Attorney, Agent, or Firm—Sherman & Shalloway

[57] ABSTRACT

A catalyst for the oxidation of propylene, said catalyst having the composition represented by the following formula $$Mo_a W_b Bi_c Fe_d A_e B_f C_g D_h O_x$$

wherein

A represents at least one element selected from the group consisting of nickel and cobalt,
B represents at least one element selected from the group consisting of alkali metals, alkaline earth metals and thallium,
C represents at least one element selected from the group consisting of phosphorus, arsenic, boron and niobium,
D represents at least one element selected from the group consisting of silicon, aluminum and titanium,
a, b, c, d, e, f, g, h, and x respectively represent the atomic ratios of Mo, W, Bi, Fe, A, B, C, D, and O,
a is from 2 to 12,
b is from 0 to 10,
the sum of a and b is 12,
c is from 0.1 to 10.0,
d is from 0.1 to 10.0,
e is from 2 to 20,
f is from 0.005 to 3.0,
g is from 0 to 4,
h is from 0.5 to 15 and
x is a number determined by the atomic valences of the individual elements, and being molded in the shape of a hollow cylinder having an outside diameter of 3.0 to 10.0 mm, an inside diameter 0.1 to 0.7 times the outside diameter and a length 0.5 to 2.0 times the outside diameter.

3 Claims, 1 Drawing Figure

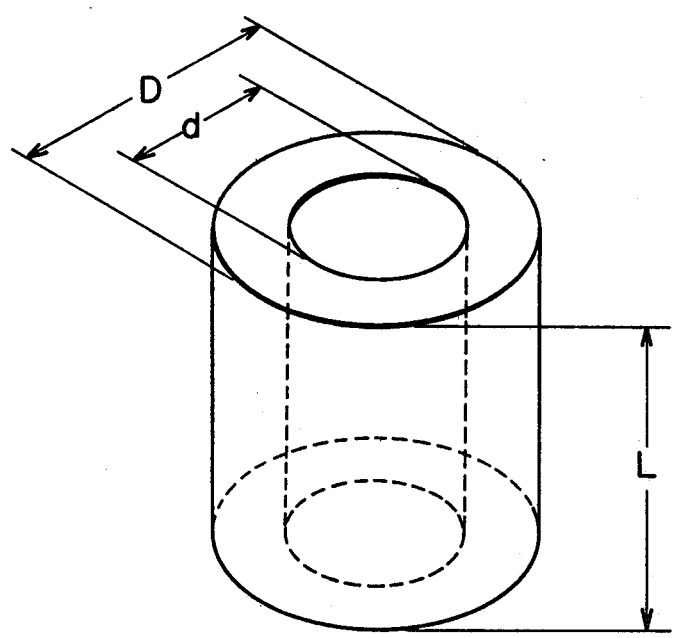

4,438,217

CATALYST FOR OXIDATION OF PROPYLENE

This invention relates to a catalyst for use in obtaining acrolein at a high selectivity and yield by the catalytic vapor-phase oxidation of propylene with air or a gas containing molecular oxygen.

Many catalysts have already been proposed for the production of acrolein by the catalytic vapor-phase oxidation of propylene, and some of them have come into industrial acceptance. Such catalysts are disclosed, for example, in the specifications of U.S. Pat. Nos. 3,907,712, 3,890,248, 3,778,386, 4,008,280, 3,970,702, and 3,761,424. The catalysts disclosed in these patent specifications are spherical or solid cylindrical molded articles of catalyst compositions based on molybdenum.

Although these catalysts are actually used in industrial operations, they are unable to give acrolein at high selectivities and yields, as described in the specific working examples in these patent documents. In actual industrial practice, the catalytic vapor-phase oxidation reaction of propylene is very exothermic to cause the formation of unusually heated high-temperature localities, called hot spots, in the catalyst layer, and the oxidation reaction proceeds excessively. Or since the height of the catalyst layer is large and the pressure in the catalyst layer varies from the inlet of the layer toward its outlet, the reaction becomes remote from an ideal one.

It is an object of this invention therefore to eliminate such disadvantages, and to provide a catalyst for producing acrolein at a high selectivity and a high yield.

The present inventors have found that the above object is achieved by a molded article having a specified shape different from the spherical or solid cylindrical shape in the prior art, which is obtained from a catalyst composition having specified constituent proportions.

BRIEF DESCRIPTION OF THE DRAWING

The accompanying drawing is a perspective view for illustrating the catalyst of this invention.

According to this invention, there is provided a catalyst for the oxidation of propylene, said catalyst having the composition represented by the following general formula $$Mo_aW_bBi_cFe_dA_eB_fC_gD_hO_x$$

wherein

A represents at least one element selected from the group consisting of nickel and cobalt, B represents at least one element selected from the group consisting of alkali metals, alkaline earth metals and thallium, C represents at least one element selected from the group consisting of phosphorus, arsenic, boron and niobium, D represents at least one element selected from the group consisting of silicon, aluminum and titanium, a, b, c, d, e, f, g, h, and x respectively represent the atomic ratios of Mo, W, Bi, Fe, A, B, C, D, and O, a is from 2 to 12, b is from 0 to 10, the sum of a and b is 12, c is from 0.1 to 10.0, preferably from 0.5 to 5.0, d is from 0.1 to 10.0, preferably from 0.5 to 5.0, e is from 2 to 20, preferably from 3 to 15, f is from 0.005 to 3.0, preferably from 0.01 to 2.5, g is from 0 to 4, preferably from 0 to 2, h is from 0.5 to 15, preferably from 1 to 10, and x is a number determined by the atomic valences of the individual elements, and being molded in the shape of a hollow cylinder having an outside diameter D of from 3.0 to 10.0 mm, an inside diameter d 0.1 to 0.7 times the outside diameter and a length L 0.5 to 2.0 times the outside diameter.

If L is smaller than D, L is properly termed "thickness" rather than "length", and the shape of the molded catalyst is properly termed the shape of a "ring" rather than the "hollow cylinder".

The catalyst of this invention is advantageous not only for the production of acrolein from propylene, but also for use as a first-stage catalyst in the process of producing acrylic acid, because the total yield of acrolein and acrylic acid is very high.

The catalyst of this invention has the advantage that since its shape is a hollow cylinder or a ring, its geometrical surface area increases, and with it, the conversion of propylene increases, and that acrolein formed in the pores of the catalyst diffuses therein more rapidly than in the case of a solid cylindrical catalyst, and the consecutive reaction from acrolein to acrylic acid, acetic acid, carbon dioxide and carbon monoxide is reduced.

According to the catalyst of this invention, the pressure drop in the catalyst layer decreases and the cost of the electric power consumption of blowers in industrial production can be reduced, although this can naturally be expected from the hollow cylindrical or ring-like shape of the catalyst of this invention. Example 8 and Comparative Example 1 given hereinbelow show that the pressure drop in a layer of a cylindrical catalyst having a diameter of 6.0 mm and a length of 6.6 mm is on the same level as that in a layer of a hollow cylindrical catalyst having an outside diameter (D) of 5.0 mm, an inside diameter (d) of 2.0 mm and a length (L) of 5.5 mm. Thus, according to this invention, it is possible to reduce the size of the catalyst particles to a greater extent and thus increase the geometrical surface area of the catalyst, and therefore to correspondingly obtain higher activity and higher yields.

The catalyst of this invention further has the advantage of possessing a long active lifetime. Since it is of a hollow cylindrical or a ring-like shape, the effect of removing heat from the unusually high-temperature localities, or the hot spots, is increased and the heat generation by a consecutive reaction to acrylic acid, acetic acid, carbon dioxide and carbon monoxide is reduced. Consequently, the temperature of the hot spots decreases, the rate of increase of the pressure drop caused by the sublimation of molybdenum, one catalyst ingredient, during the reaction is reduced, and the life of the catalyst is prolonged.

The catalyst of this invention is prepared by known methods. For example, a catalyst composition in the form of a powder or clay obtained by precipitation, kneading, etc., after, if desired, adding small amounts of carbon black, stearic acid, starch, polyacrylic acid, a mineral or vegetable oil, water, etc., is molded into a hollow cylindrical or a ring-like shape by a tableting machine, an extrusion molding machine, etc. and calcined in a stream of air or nitrogen at a temperature of 150° to 450° C. to give a catalyst as a catalyst oxide of the composition .

Starting materials for the catalyst of this invention are desirably compounds which can be converted to oxides in the catalyst preparation process as described above.

Examples include the nitrates, ammonium salts, organic acid salts, hydroxides, oxides, metallic acids, and ammonium salts of the metal acids. Illustrative of the alkali metal are lithium, sodium, potassium, rubidium and cesium. Potassium, rubidium and cesium are preferred. Examples of the alkaline earth metal are magnesium, calcium, barium and strontium. Calcium and barium are preferred.

In the present invention, the shape of the catalyst is of utmost importance. Comparative Examples show that if the catalyst has the composition specified above but is not in the hollow cylindrical or ring-like shape specified above, it cannot exhibit the performance desired in this invention. The catalyst of this invention exhibits a very good catalytic performance when it is molded into such a hollow cylindrical shape that the average thickness, i.e. $(D-d)/2$, is from 1.0 to 4.0 mm. Preferably, the wall thickness is at least 1.0 mm because too small a wall thickness will result in a reduction in the strength of the catalyst.

Propylene is oxidized in the vapor phase in the presence of the catalyst of this invention by passing a gaseous mixture composed of 1 to 10% by volume of propylene, 5 to 18% by volume of molecular oxygen, 0 to 60% by volume of steam and 20 to 70% by volume of an inert gas (such as nitrogen or carbon dioxide) over the catalyst at a temperature of 250° to 450° C. and a pressure of atmospheric pressure to 10 atmospheres with a contact time of 0.5 to 10.0 seconds.

The following Examples and Comparative Examples illustrate the present invention more specifically. It should be understood however that the invention is by no means limited to these specific examples.

The conversion, selectivity and one-pass yield, as used in this invention, are defined as follows:

$$\text{Conversion (\%)} = \frac{\text{Moles of propylene reacted}}{\text{Moles of propylene fed}} \times 100$$

$$\text{Selectivity (\%)} = \frac{\text{Moles of the unsaturated carbonyl formed}}{\text{Moles of propylene reacted}} \times 100$$

$$\text{One-pass yield (\%)} = \frac{\text{Moles of the unsaturated carbonyl formed}}{\text{Moles of propylene fed}} \times 100$$

EXAMPLE 1

Ammonium molybdate (2124 g) and 648 g of ammonium paratungstate were dissolved in 3,000 ml of distilled water heated with stirring. The resulting solution is designated as solution A.

Separately, 1400 g of cobalt nitrate was dissolved in 400 ml of distilled water; 486 g of ferric nitrate was dissolved in 400 ml of distilled water; and 584 g of bismuth nitrate was added to 600 ml of distilled water acidified with 120 ml of concentrated nitric acid.

A mixture of the three solutions was added dropwise to the solution A, and subsequently, a solution of 488 g of silica sol containing 20% by weight of silica and 4.04 g of potassium hydroxide in 300 ml of distilled water was added.

The resulting suspension was heated with stirring and evaporated to dryness, pulverized, and then molded into a hollow cylindrical shape having an outside diameter (D) of 6.0 mm, an inside diameter (d) of 1.0 mm, and a length (L) of 6.6 mm. The molded product was calcined in the air at 450° C. for 6 hours. The resulting catalyst had the following elemental composition excepting oxygen (atomic ratio).

$$Co_4Bi_1Fe_1W_2Mo_{10}Si_{1.35}K_{0.06}$$

The resulting catalyst (1500 ml) was filled in a steel reaction tube having a diameter of 25.4 mm to a catalyst layer length of 2960 mm. At a reaction temperature of 320° C., a gaseous mixture composed of 7% by volume of propylene, 12.6% by volume of oxygen, 10% by volume of steam and 70.4% by volume of nitrogen was introduced into the reaction tube and reacted with a contact time of 2.25 seconds. The pressure drop and ΔT (the difference between the reaction temperature and the temperature of the hot spot) during the reaction, and the yields of the products are shown in Table 1.

EXAMPLE 2

The procedure of Example 1 was repeated except that the inside diameter of the catalyst was changed to 2.0 mm. The pressure drop and ΔT during the reaction, and the yields of the products are shown in Table 1.

EXAMPLE 3

The procedure of Example 1 was repeated except that the inside diameter of the catalyst was changed to 3.0 mm. The pressure drop and ΔT during the reaction, and the yields of the products are shown in Table 1.

COMPARATIVE EXAMPLE 1

The catalyst composition prepared in Example 1 was molded into a solid cylindrical shape having diameter of 6.0 mm and a length of 6.6 mm, and calcined in the same way as in Example 1. By using the resulting catalyst, the same reaction as in Example 1 was carried out. The pressure drop and ΔT during the reaction, and the yields of the products are shown in Table 1.

EXAMPLE 4

A catalyst molded in the shape of a hollow cylinder having an outside diameter (D) of 4.0 mm, an inside diameter (d) of 1.0 mm and a length (L) of 4.4 mm was prepared in the same way as in Example 1 except that thallium nitrate and barium nitrate were used instead of potassium hydroxide. The resulting catalyst had the following elemental composition (atomic ratio) excepting oxygen.

$$Mo_{10}Bi_1Fe_{1.5}Co_4Si_{1.35}W_2Tl_{0.04}Ba_{0.05}$$

By using this catalyst, the same reaction as in Example 1 was carried out.

The pressure drop and ΔT during the reaction, and the yields of the products are shown in Table 1.

COMPARATIVE EXAMPLE 2

The catalyst composition prepared in Example 4 was molded into the shape of a solid cylinder having a diameter of 4.0 mm and a length of 4.4 mm, and calcined in the same way as in Example 1. By using the resulting catalyst, the same reaction as in Example 1 was carried out.

The pressure drop and ΔT during the reaction, and the yields of the products are shown in Table 1.

EXAMPLE 5

A catalyst molded in the shape of a hollow cylinder having an outside diameter (D) of 8.0 mm, an inside diameter (d) of 3.0 mm and a length (L) of 8.8 mm was prepared in the same way as in Example 1 except that cesium nitrate was used instead of potassium hydroxide, and titanium dioxide was added together with 20 wt.% silica sol. The resulting catalyst had the following elemental composition (atomic ratio) excepting oxygen.

$$Mo_{10}Bi_1Fe_1Co_4Si_{1.35}W_2Cs_{0.02}Ti_{1.0}$$

By using this catalyst, the same reaction as in Example 1 was carried out.

The pressure drop and ΔT during the reaction, and the yields of the products are shown in Table 1.

COMPARATIVE EXAMPLE 3

The catalyst composition prepared in Example 5 was molded into the shape of a solid cylinder having a diameter of 8.0 mm and a length of 8.8 mm, and calcined in the same way as in Example 5. By using the resulting catalyst, the same reaction as in Example 1 was carried out.

The pressure drop and ΔT during the reaction, and the yields of the products are shown in Table 1.

resulting catalyst, the same reaction as in Example 1 was carried out.

The pressure drop and ΔT during the reaction, and the yields of the products are shown in Table 2.

EXAMPLE 7

A catalyst molded into the shape of a hollow cylinder having an outside diameter (D) of 6.0 mm, an inside diameter (d) of 2.0 mm, and a length (L) of 6.6 mm was prepared in the same way as in Example 1 except that calcium nitrate was used instead of potassium hydroxide, and niobium pentoxide was added after the addition of silica sol and calcium nitrate. The resulting catalyst had the following elemental composition (atomic ratio) excepting oxygen.

$$Co_4Bi_1Fe_1Mo_{10}W_2Si_{1.35}Ca_{0.06}Nb_{0.5}$$

By using this catalyst, the same reaction as in Example 1 was carried out.

The pressure drop and ΔT during the reaction, and the yields of the products are shown in Table 2.

TABLE 1

| Example (Ex.) or Comparative Example (CEx.) | Shape of the catalyst | | | Conversion of propylene (mole %) | Selectivity (mole %) | | One-pass yield (mole %) | | ΔT (°C.) | Pressure drop (mmHg) |
| --- | --- | --- | --- | --- | --- | --- | --- | --- | --- | --- |
| | D (mm) | d (mm) | L (mm) | | Acrolein | Acrylic acid | Acrolein | Acrylic acid | | |
| Ex. 1 | 6.0 | 1.0 | 6.6 | 96.2 | 86.6 | 10.2 | 83.3 | 9.8 | 68 | 130 |
| Ex. 2 | 6.0 | 2.0 | 6.6 | 96.0 | 90.6 | 6.8 | 87.0 | 6.5 | 60 | 110 |
| Ex. 3 | 6.0 | 3.0 | 6.6 | 95.5 | 92.3 | 5.2 | 88.1 | 5.0 | 51 | 90 |
| CEx. 1 | 6.0 | — | 6.6 | 95.5 | 83.9 | 12.8 | 80.1 | 12.2 | 75 | 140 |
| Ex. 4 | 4.0 | 1.0 | 4.4 | 98.0 | 88.7 | 8.1 | 86.9 | 7.9 | 74 | 170 |
| CEx. 2 | 4.0 | — | 4.4 | 96.8 | 84.6 | 11.5 | 81.9 | 11.1 | 86 | 210 |
| Ex. 5 | 8.0 | 3.0 | 8.8 | 91.5 | 90.4 | 6.6 | 82.7 | 6.0 | 40 | 65 |
| CEx. 3 | 8.0 | — | 8.8 | 90.3 | 85.6 | 10.2 | 77.3 | 9.2 | 53 | 80 |

EXAMPLE 6

A catalyst molded in the shape of a hollow cylinder having an outside diameter (D) of 6.0 mm, an inside diameter of 2.0 mm and a length (L) of 6.6 mm was prepared in the same way as in Example 1 except that strontium nitrate was used instead of potassium hydroxide. This catalyst had the following elemental composition (atomic ratio) excepting oxygen.

COMPARATIVE EXAMPLE 2

The catalyst composition prepared in Example 7 was molded into the shape of a solid cylinder having a diameter of 6.0 mm and a length of 6.6 mm, and calcined in the same way as in Example 7. By using the resulting catalyst, the same reaction as in Example 1 was carried out.

The pressure drop and ΔT during the reaction, and the yields of the products are shown in Table 2.

TABLE 2

| Example (Ex.) or Comparative Example (CEx.) | Shape of the catalyst | | | Conversion of propylene (mole %) | Selectivity (mole %) | | One-pass yield (mole %) | | ΔT (°C.) | Pressure drop (mmHg) |
| --- | --- | --- | --- | --- | --- | --- | --- | --- | --- | --- |
| | D (mm) | d (mm) | L (mm) | | Acrolein | Acrylic acid | Acrolein | Acrylic acid | | |
| Ex. 6 | 6.0 | 2.0 | 6.6 | 95.4 | 90.5 | 6.5 | 86.3 | 6.2 | 55 | 110 |
| CEx. 4 | 6.0 | — | 6.6 | 94.8 | 84.2 | 11.8 | 79.8 | 11.2 | 70 | 140 |
| Ex. 7 | 6.0 | 2.0 | 6.6 | 95.9 | 89.2 | 7.8 | 85.5 | 7.5 | 60 | 110 |
| CEx. 5 | 6.0 | — | 6.6 | 95.2 | 82.8 | 13.3 | 78.8 | 12.7 | 75 | 140 |

$$Co_4Bi_1Fe_1Mo_{10}W_2Si_{1.35}Sr_{0.06}$$

By using the resulting catalyst, the same reaction as in Example 1 was carried out.

The pressure drop and ΔT during the reaction, and the yields of the products are shown in Table 2.

COMPARATIVE EXAMPLE 4

The catalyst composition prepared in Example 6 was molded into the shape of a solid cylinder having a diameter of 6.0 mm and a length of 6.6 mm. By using the

EXAMPLE 8

The same catalyst composition as in Example 1 was molded into the shape of a hollow cylinder having an outside diameter (D) of 5.0 mm, an inside diameter (d) of 2.0 mm and a length (L) of 5.5 mm. By using this catalyst, the same reaction as in Example 1 was carried out. The pressure drop during the reaction was the same as in Comparative Example 1. The ΔT and the yields of the products are shown in Table 3.

TABLE 3

| Example (Ex.) or Comparative Example (CEx.) | Shape of the catalyst | | | Conversion of propylene (mole %) | Selectivity (mole %) | | One-pass yield (%) | | | ΔT (°C.) |
|---|---|---|---|---|---|---|---|---|---|---|
| | D (mm) | d (mm) | L (mm) | | Acrolein | Acrylic acid | Acrolein | Acrylic acid | Total | |
| Ex. 8 | 5.0 | 2.0 | 5.5 | 97.2 | 89.0 | 8.3 | 86.5 | 8.1 | 94.6 | 70 |
| CEx. 1 | 6.0 | — | 6.6 | 95.5 | 83.9 | 12.6 | 80.1 | 12.0 | 92.1 | 75 |

EXAMPLE 9

A catalyst molded into the shape of a hollow cylinder having an outside diameter (D) of 6.0 mm, an inside diameter (d) of 2.0 mm and a length (L) of 6.6 mm was prepared in the same way as in Example 1 except that nickel nitrate was added together with cobalt nitrate, rubidium nitrate was used in place of potassium hydroxide, phosphoric acid was added instead of ammonium paratungstate, and that the calcination was carried out at 500° C. for 6 hours. The resulting catalyst had the following elemental composition (atomic ratio) excepting oxygen.

$Mo_{12}Bi_1Fe_2Ni_1Co_3Si_{4.7}P_{1.0}Rb_{0.1}$

By using the resulting catalyst, the same reaction as in Example 1 was carried out.

The pressure drop and ΔT during the reaction, and the yields of the products are shown in Table 4.

COMPARATIVE EXAMPLE 6

The catalyst composition prepared in Example 9 was molded into the shape of a solid cylinder having a diameter of 6.0 mm and a length of 6.6 mm, and calcined in the same way as in Example 9. By using the resulting catalyst, the same reactions as in Example 1 was carried out.

The pressure drop and ΔT during the reaction, and the yields of the products are shown in Table 4.

EXAMPLE 10

A catalyst molded in the shape of a hollow cylinder having an outside diameter (D) of 6.0 mm, and inside diameter (d) of 2.0 mm and a length (L) of 6.6 mm was prepared in the same way as in Example 1 except that nickel nitrate and aluminum nitrate were added together with cobalt nitrate, boric acid was used instead of ammonium paratungstate, and the calcination was carried out at 500° C. for 6 hours. The resulting catalyst had the following elemental composition (atomic ratio) excepting oxygen.

$Mo_{12}Bi_1Fe_2Ni_1Co_3Si_{4.7}B_{2.0}K_{0.2}Al_{1.0}$

By using the resulting catalyst, the same reaction as in Example 1 was carried out.

The pressure drop and ΔT during the reaction, and the yields of the products are shown in Table 4.

COMPARATIVE EXAMPLE 7

The catalyst composition prepared in Example 10 was molded into the shape of a solid cylinder having a diameter of 6.0 mm and a length of 6.6 mm, and calcined in the same way as in Example 10. By using the resulting catalyst, the same reaction as in Example 1 was carried out.

The pressure drop and ΔT during the reaction, and the yields of the products are shown in Table 4.

TABLE 4

| Example (Ex.) or Comparative Example (CEx.) | Shape of the catalyst | | | Conversion of propylene (mole %) | Selectivity (mole %) | | One-pass yield (mole %) | | ΔT (°C.) | Pressure drop (mmHg) |
|---|---|---|---|---|---|---|---|---|---|---|
| | D (mm) | d (mm) | L (mm) | | Acrolein | Acrylic acid | Acrolein | Acrylic acid | | |
| Ex. 9 | 6.0 | 2.0 | 6.6 | 94.5 | 84.7 | 10.1 | 80.0 | 9.5 | 76 | 110 |
| CEx. 6 | 6.0 | — | 6.6 | 94.0 | 78.9 | 13.3 | 74.2 | 12.5 | 97 | 140 |
| Ex. 10 | 6.0 | 2.0 | 6.6 | 93.4 | 80.0 | 10.8 | 74.7 | 10.1 | 70 | 110 |
| CEx. 7 | 6.0 | — | 6.6 | 92.8 | 76.1 | 13.7 | 70.6 | 12.7 | 85 | 140 |

EXAMPLE 11

Subsequent of the oxidation reaction of propylene described in Example 2, a second-stage reaction for the production of acrylic acid was carried out in the following manner.

1500 ml of a catalyst prepared in accordance with the description of Example 1 of U.S. Pat. No. 3,833,649 and composed of a catalytic oxide having the elemental composition (atomic ration excepting oxygen) $Mo_{12}V_{4.6}Cu_{2.2}Cr_{0.6}W_{2.4}$ deposited on alumina was filled in a steel reaction tube having a diameter of 25.4 mm to a catalyst layer length of 3000 mm, and a reactor in which the temperature of the heating medium was adjusted to 255° C. was connected to the tube. The reaction gas obtained in Example 2 was rapidly cooled to 250° C., and directly fed into the reactor. At the exit of the second-stage reactor, the conversion of propylene was 96.8%, the one-pass yield of acrylic acid was 90.4%, and the amount of remaining acrolein was trace.

What is claimed is:

1. A catalyst for the oxidation of propylene, said catalyst having the composition represented by the following formula $Mo_aW_bBi_cFe_dA_eB_fC_gD_hO_x$ wherein
A represents at least one element selected from the group consisting of nickel and cobalt,
B represents at least one element selected from the group consisting of alkali metals, alkaline earth metals and thallium,
C represents at least one element selected from the group consisting of phosphorus, arsenic, boron and niobium,
D represents at least one element selected from the group consisting of silicon, aluminum and titanium, a, b, c, d, e, f, g, h, and x respectively represent the atomic ratios of Mo, W, Bi, Fe, A, B, C, D, and O, a is from 2 to 12 b is from 0 to 10, the sum of a and b is 12, c is from 0.1 to 10.0, d is from 0.1 to 10.0, e is from 2 to 20, f is from 0.005 to 3.0, g is from 0 to 4, h is from 0.5 to 15 and X is a number determined by the atomic valences of the individual elements, and being molded in the shape of a hollow cylinder having an outside diameter of 3.0 to 10.0 mm, an inside diameter 0.1 to 0.7 times the outside diameter and a length 0.5 to 2.0 times the outside diameter.

2. The catalyst of claim 1 wherein $(D-d)/2$ where D is the outside diameter of the hollow cylinder and d is the inside diameter of the hollow cylinder is from 1.0 to 4.0 mm.

3. The catalyst of claim 1 wherein c is from 0.5 to 5.0, d is from 0.5 to 5.0, e is from 3 to 15, f is from 0.01 to 2.5, g is from 0 to 2, and h is from 1 to 10.

* * * * *

UNITED STATES PATENT AND TRADEMARK OFFICE
CERTIFICATE OF CORRECTION

PATENT NO. : 4,438,217
DATED     : March 20, 1984
INVENTOR(S) : Masahiro Takata et al It is certified that error appears in the above-identified patent and that said Letters Patent is hereby corrected as shown below:

Assignee: delete "Nippin Shokubai Kagako Kogyo Co., Ltd." and insert -- Nippon Shokubai Kagaku Kogyo Co., Ltd. --

Signed and Sealed this

Eleventh Day of September 1984

[SEAL]

Attest:

GERALD J. MOSSINGHOFF

Attesting Officer    Commissioner of Patents and Trademarks

REEXAMINATION CERTIFICATE (1185th)
United States Patent
Takata et al.

[11] B1 4,438,217
[45] Certificate Issued Jan. 9, 1990

[54] CATALYST FOR OXIDATION OF PROPYLENE

[75] Inventors: Mashiro Takata; Ryuji Aoki; Takahisa Sato, all of Himeji, Japan

[73] Assignee: Nippon Shokubai Kagak Kogyo Co., Ltd., Osaka, Japan

Reexamination Request:
No. 90/001,677, Dec. 22, 1988

Reexamination Certificate for:
Patent No.: 4,438,217
Issued: Mar. 20, 1984
Appl. No.: 454,611
Filed: Dec. 30, 1982

[30] Foreign Application Priority Data

Jan. 6, 1982 [JP] Japan .................................. 57-406

[51] Int. Cl.$^4$ .................. B01J 21/08; B01J 23/78; B01J 23/84; B01J 23/88
[52] U.S. Cl. .................................. 502/205; 502/212; 502/243; 502/246; 502/263; 502/306; 502/309; 502/311; 502/527; 568/479
[58] Field of Search ............... 502/205, 212, 243, 246, 502/263, 306, 309, 311, 527; 568/479

[56] References Cited

FOREIGN PATENT DOCUMENTS

| | | |
|---|---|---|
| 0015569 | of 1980 | European Pat. Off. |
| 1667266 | of 1972 | Fed. Rep. of Germany |
| 2228266 | of 1973 | Fed. Rep. of Germany |
| 2255225 | of 1973 | Fed. Rep. of Germany |
| 2510994 | of 1976 | Fed. Rep. of Germany |
| 3006894 | of 1980 | Fed. Rep. of Germany |
| 3113179 | of 1982 | Fed. Rep. of Germany |
| 141842 | of 1981 | Japan |
| 6709671 | of 1958 | Netherlands |
| 1188675 | of 1970 | United Kingdom |
| 1373317 | of 1974 | United Kingdom |
| 1463174 | of 1977 | United Kingdom |
| 2042530 | of 1980 | United Kingdom |
| 2044764 | of 1980 | United Kingdom |

OTHER PUBLICATIONS

Ulmanns Encyclopedia of Industrial Chemistry-4th Revised Enlarged Edition-vol. 13-pp. 537-9, 569 (1977).
Kasaoka et al.-Chem. Engineering (Japan)-vol. 30, No. 2, Feb. 1966.

*Primary Examiner*—William J. Shine

[57] ABSTRACT

A catalyst for the oxidation of propylene, said catalyst having the composition represented by the following formula $$Mo_a W_b Bi_c Fe_d A_e B_f C_g D_h O_x$$

wherein
A represents at least one element selected from the group consisting of nickel and cobalt,
B represents at least one element selected from the group consisting of alkali metals, alkaline earth metals and thallium,
C represents at least one element selected from the group consisting of phosphorus, arsenic, boron and niobium,
D represents at least one element selected from the group consisting of silicon, aluminum and titanium,
a, b, c, d, e, f, g, h, and x respectively represent the atomic ratios of Mo, W, Bi, Fe, A, B, C, D, and O,
a is from 2 to 12,
b is from 0 to 10,
the sum of a and b is 12,
c is from 0.1 to 10.0,
d is from 0.1 to 10.0,
e is from 2 to 20,
f is from 0.005 to 3.0,
g is from 0 to 4,
h is from 0.5 to 15 and
x is a number determined by the atomic valences of the individual elements, and being molded in the shape of a hollow cylinder having an outside diameter of 3.0 to 10.0 mm, an inside diameter 0.1 to 0.7 times the outside diameter and a length 0.5 to 2.0 times the outside diameter.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent but has been deleted and is no longer a part of the patent; matter printed in italics indicates additions made to the patent.

AS A RESULT OF REEXAMINATION, IT HAS BEEN DETERMINED THAT:

The patentability of claims 1-3 is confirmed.

New claims 4-7 are added and determined to be patentable.

*4. The catalyst of claim 1 wherein the catalyst is in the form of a hollow cylinder having an outside diameter of 6 millimeters, an inside diameter of 1.0 millimeter, and a length of 6.6 millimeters.*

*5. The catalyst of claim 1 wherein the catalyst is in the form of a hollow cylinder having an outside diameter of 8.0 millimeters, an inside diameter of 3.0 millimeters, and a length of 8.8 millimeters.*

*6. The catalyst of claim 1 wherein the catalyst is in the form of a hollow cylinder having an outside diameter of 6 millimeters, an inside diameter of 2.0 millimeters, and a length of 6.6 millimeters.*

*7. The catalyst of claim 1 wherein the catalyst is in the form of a hollow cylinder having an outside diameter of 6 millimeters, an inside diameter of 3.0 millimeters, and a length of 6.6 millimeters.*

* * * * *